(12) United States Patent
Strobel

(10) Patent No.: US 7,789,562 B2
(45) Date of Patent: Sep. 7, 2010

(54) CALIBRATION OF A MULTI-PLANE X-RAY UNIT

(75) Inventor: Norbert Strobel, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/472,433

(22) Filed: May 27, 2009

(65) Prior Publication Data

US 2009/0296893 A1 Dec. 3, 2009

(30) Foreign Application Priority Data

May 28, 2008 (DE) ...................... 10 2008 025 538

(51) Int. Cl.
*G01D 18/00* (2006.01)
(52) U.S. Cl. .................................... 378/207
(58) Field of Classification Search .................... 378/4, 378/8, 9, 19, 98.8, 64, 207; 600/407, 424
See application file for complete search history.

(56) References Cited

U.S. PATENT DOCUMENTS

| | | | | |
|---|---|---|---|---|
| 6,405,071 B1 * | 6/2002 | Analoui | ...................... | 600/425 |
| 6,549,607 B1 * | 4/2003 | Webber | .......................... | 378/8 |
| 6,731,283 B1 * | 5/2004 | Navab | ......................... | 345/424 |
| 6,856,827 B2 | 2/2005 | Seeley et al. | | |
| 2004/0097805 A1 | 5/2004 | Verard et al. | | |
| 2004/0138548 A1 | 7/2004 | Strommer et al. | | |
| 2005/0033149 A1 | 2/2005 | Strommer et al. | | |
| 2006/0064006 A1 | 3/2006 | Strommer et al. | | |
| 2009/0067583 A1 * | 3/2009 | Vogt et al. | ................... | 378/207 |
| 2009/0074150 A1 * | 3/2009 | Jaffray et al. | ................ | 378/197 |

FOREIGN PATENT DOCUMENTS

DE 10114099 A1 10/2002
EP 1346687 B1 9/2003

* cited by examiner

*Primary Examiner*—Irakli Kiknadze

(57) ABSTRACT

For calibrating a multi-plane X-ray unit, an internal matrix mapping coordinate system internal to the unit onto coordinate system of a first radiographic plane is predefined in a reference projection geometry. An external matrix mapping coordinate system external to the unit onto coordinate system of the first plane is determined from image data captured by the first plane at calibration points and coordinates of the calibration points. An external matrix mapping coordinate system external to the unit onto coordinate system of a second radiographic plane is determined from image data captured by the second plane at the calibration points and the coordinates of the calibration points. A measure of position of the second plane with respect to coordinate system internal to the unit or with respect to the first plane is determined from the internal and external matrix of the first plane and the external matrix of the second plane.

12 Claims, 3 Drawing Sheets

CALIBRATION OF A MULTI-PLANE X-RAY UNIT

CROSS REFERENCE TO RELATED APPLICATIONS

This application claims priority of German application No. 10 2008 025 538.6 filed May 28, 2008, which is incorporated by reference herein in its entirety.

FIELD OF THE INVENTION

The invention relates to a method for calibrating a multi-plane X-ray unit. The invention also relates to a calibration unit for executing the method as well as a multi-plane X-ray unit having such a calibration unit.

BACKGROUND OF THE INVENTION

An X-ray unit intended in particular for medical use, which has a plurality of radiographic planes offset with respect to one another, is referred to as a multi-plane X-ray unit. In this situation, each radiographic plane is essentially formed by an—in particular two-dimensional—X-ray detector. In most cases, a separate X-ray source is moreover associated with each radiographic plane.

X-ray units having two radiographic planes—also referred to as bi-plane or dual-source units—are used today in particular in 3D imaging (computer tomography, rotational angiography, etc.) or for the purpose of instrument navigation accompanying operations. The two radiographic planes of such units are in part, with respect to a central ray perpendicular to the particular radiographic plane, arranged offset from one another by a fixed angle. In this situation, the two radiographic planes can generally be rotated together around a common isocenter. On the other hand, for instrument navigation in particular, units having two emitter/detector pairs capable of independent movement are used. In this case, each of these emitter/detector pairs is as a general rule mounted on a separate C-arm.

When using a multi-plane X-ray unit it is possible on the one hand to produce three-dimensional image data sets, in particular so-called tomograms, of an object under examination in a shorter time than in the presence of only one radiographic plane. For three-dimensional localization of objects in the radiographic area of the X-ray unit, in particular for the purpose of instrument localization and navigation, the capture of an individual X-ray image by using two radiographic planes is also already basically sufficient such that a rotation of the radiographic planes is not required.

Error-free evaluation of the image data delivered by a multi-plane X-ray unit and a precise localization does however require a precise knowledge of the orientation of the radiographic planes in the space. This positioning of the radiographic planes is determined as a rule through calibration of the multi-plane X-ray unit. Such a calibration is performed in particular during commissioning of the unit. In order to avoid a maladjustment of the unit during actual operation, or at least to recognize such maladjustment, it may additionally be necessary to repeat the calibration at regular intervals during operation of the unit. In this case one also speaks of recalibration. In the case of units having independently moveable radiographic planes, such as double C-arm units for example, the problem can exist that for reasons of design only one of the radiographic planes is capable of stable calibration. In the case of such units, the second radiographic plane often needs to be frequently recalibrated, sometimes with a considerable degree of adjustment.

SUMMARY OF THE INVENTION

The object of the invention is to set down a precise and easily executed, in particular easily automatable, method for such a calibration of a multi-plane X-ray unit. The object of the invention is also to set down an especially suitable device for automatically executing the method.

With regard to the method, this object is achieved according to the invention by the features described in the claims.

According to the method, it is assumed that an internal spatial coordinate system is defined with respect to the multi-plane X-ray unit. It is furthermore assumed that for each radiographic plane of the unit an image coordinate system is defined, which characterizes the position of an image point within the radiographic plane, in particular therefore within the detector surface associated with the radiographic plane. Finally, it is assumed that at least with respect to a first radiographic plane of the unit at least one reference projection geometry exists, for which an internal projection matrix is predefined internally to the unit, which maps the internal spatial coordinate system onto the image coordinate system of the first radiographic plane. A calculation rule is therefore designated as the internal projection matrix of the first radiographic plane, by means of which rule the coordinates of an image point of the first radiographic plane (in units of the associated image coordinate system) can be calculated from the internal spatial coordinates of the particular point in space which is projected into this image point in the reference projection geometry.

According to the method, the reference projection geometry (or one of the reference projection geometries) will now be set with respect to the first radiographic plane and under this setting image data for a number of calibration points will be captured. In this situation, a calibration point is generally understood to be a point in space capable of being imaged by X-ray photography. Such a calibration point is implemented in particular by means of a point object capable of being imaged by X-ray photography, which is arranged at a certain spatial position. A point object is in turn understood to be an approximately punctiform object in terms of the imaging technology or an approximately punctiform part of a larger object in terms of the imaging technology, for example the tip of a medical instrument, etc. By definition therefore, a calibration point is formed by the imageable point object in combination with a particular spatial position. The same point object can thus also be used in order to generate a plurality of calibration points if it is imaged at different times in different spatial positions.

Furthermore, according to the method, from the image data for the calibration points generated by means of the first radiographic plane in the reference projection geometry and from the coordinates of these calibration points an external projection matrix, which maps the external spatial coordinate system onto the image coordinate system of the first radiographic plane, is determined with respect to a spatial coordinate system external to the unit.

In a further method step, image data for the same calibration points is captured by means of a second radiographic plane of the unit, whereby from this image data and the coordinates of the calibration points an external projection matrix, which maps the external spatial coordinate system onto the image coordinate system of the second radiographic plane, is determined with respect to the external spatial coordinate system.

Finally, on the basis of the (previously known) internal projection matrix of the first radiographic plane, the external projection matrix of the first radiographic plane (calculated according to the method) as well as the (likewise calculated according to the method) external projection matrix of the second radiographic plane, a measure of the position of the second radiographic plane with respect to the internal spatial coordinate system or with respect to the first radiographic plane is determined.

The invention is not restricted to the order in which the method steps described above are stated. Rather, the order of these method steps is—as far as possible—freely selectable within the scope of the invention. In particular, the calibration points can be captured basically simultaneously or in any desired order in succession by means of the two radiographic planes. The calculation of the external projection matrixes of the first and second radiographic planes can also take place simultaneously or in any desired order in succession.

The advantage of the method described above consists in particular in the fact that—in particular with regard to the choice of the calibration points—it can be configured extremely flexibly and can thus be adapted to suit different requirements. In addition, the method enables a numerically stable and thus precise calibration of the multi-plane X-ray unit, which can be carried out by means of conventional computer systems without any appreciable loss of time. In particular, no movement or only a slight degree of movement of the multi-plane X-ray unit is required for the purpose of the calibration.

Within the scope of the invention, a plurality of variants which can be used as alternatives to one another are provided for generating the calibration points. According to a first variant, provision is made to employ a static calibration phantom for generating the calibration points, which contains a plurality of X-ray detectable point objects, whose coordinates are predefined in the external spatial coordinate system. Such a calibration phantom can in particular also be integrated into a specimen stage of the multi-plane X-ray unit. The location of the external spatial coordinate system with respect to the calibration phantom can basically be chosen at will. In particular, the origin of the external spatial coordinate system can be chosen in such a manner that it coincides with a point object of the calibration phantom. The coordinates of the point objects of the calibration phantom with respect to the external spatial coordinate system can be determined for example through measurement of the calibration phantom.

As an alternative to this, a static calibration phantom of the type described above can also be used for generating the calibration points in the situation when the coordinates of the point objects of this phantom with respect to external spatial coordinate system are not known a priori. In a corresponding variant of the method, in this situation the external spatial coordinates of the point objects of the calibration phantom are initially determined by means of the multi-plane X-ray unit. To this end, the calibration phantom is captured by means of the first radiographic plane of the unit using two different projection geometries. The coordinates of the point objects of the phantom with respect to the external spatial coordinate system are then determined from the corresponding image data of the calibration phantom through triangulation.

A third method variant is preferably employed in the situation when, in addition to the multi-plane X-ray unit, a so-called (instrument) localization device is present. Such a localization device (also referred to as tracking system) senses the position of an object to be localized—in particular a medical instrument—in the space by means of, for example, an optical, acoustic, electromagnetic or impedance-based method. For this purpose, defined detection points are frequently provided on the instrument, which can be detected by the tracking systems.

According to the last-mentioned method variant, the calibration points are generated with the aid of a point object which can be sensed by the tracking system, in particular therefore a medical instrument or part of an instrument. To this end, this object is moved in a radiographic area common to the first radiographic plane and the second radiographic plane, whereby at a plurality of successive points in time, simultaneously for the given situation, the coordinates of the object with respect to the external spatial coordinate system are determined with the aid of the localization device and image data for the object is captured with the aid of the two radiographic planes. Each of these snapshots of the localized object thus forms a calibration point. This method variant has the advantage in particular that no separate calibration phantom is required. The calibration can thus also be carried out for example while the unit is operating, in particular also imperceptibly for a unit user.

In each of the method variants described above, advantageously at least three, and preferably six or even more, calibration points are captured.

In a preferred method variant, after the determination of the external projection matrix of the first radiographic plane, a transformation rule is calculated from this and also from the (previously known) internal projection matrix of the first radiographic plane, which rule maps the external spatial coordinate system and the internal spatial coordinate system onto one another. Provided that a distortion of one of the two spatial coordinate systems can be disregarded, this transformation rule preferably has the mathematical form of a so-called rigid-body transform, in which the two spatial coordinate systems are mapped onto one another by using three rotational degrees of freedom and three translational degrees of freedom. This transformation rule is then employed by preference as an interim result for calculating the measure of the position of the second radiographic plane. As a measure of the position of the second radiographic plane an internal projection matrix is preferably calculated which maps the internal spatial coordinate system onto the image coordinate system of the second radiographic plane. Alternatively, as a measure of position it would also be possible to calculate a specification which characterizes the relative position of the second radiographic plane with respect to the first radiographic plane, for example a specification for the offset angle between the radiographic planes.

With reference to the device, the above object is achieved according to the invention by the features described in the claims. Accordingly, a calibration unit is specified which is designed in order to execute the method described above in one of its variants. With regard to this calibration unit, it is in particular a software component of control software for the multi-plane X-ray unit which is set up in such a manner in terms of programming that when it is carried out the method according to the invention is executed automatically. As an alternative to this, the calibration unit can also be configured in the form of a hardware unit with software installed on it, for example taking the form of a correspondingly programmed microcontroller or a plug-in card for a control computer of the multi-plane X-ray unit. In each of these embodiments the calibration unit is optionally present as an integral component of the multi-plane X-ray unit or as a separate product which can for example constitute an additional module or a conversion kit for an existing multi-plane X-ray unit.

BRIEF DESCRIPTION OF THE DRAWINGS

Exemplary embodiments of the invention will be described in detail in the following with reference to a drawing. In the drawings.

Parts and variables corresponding to one another are always provided with the same reference characters in all the figures.

DETAILED DESCRIPTION OF THE INVENTION

Figure 1:
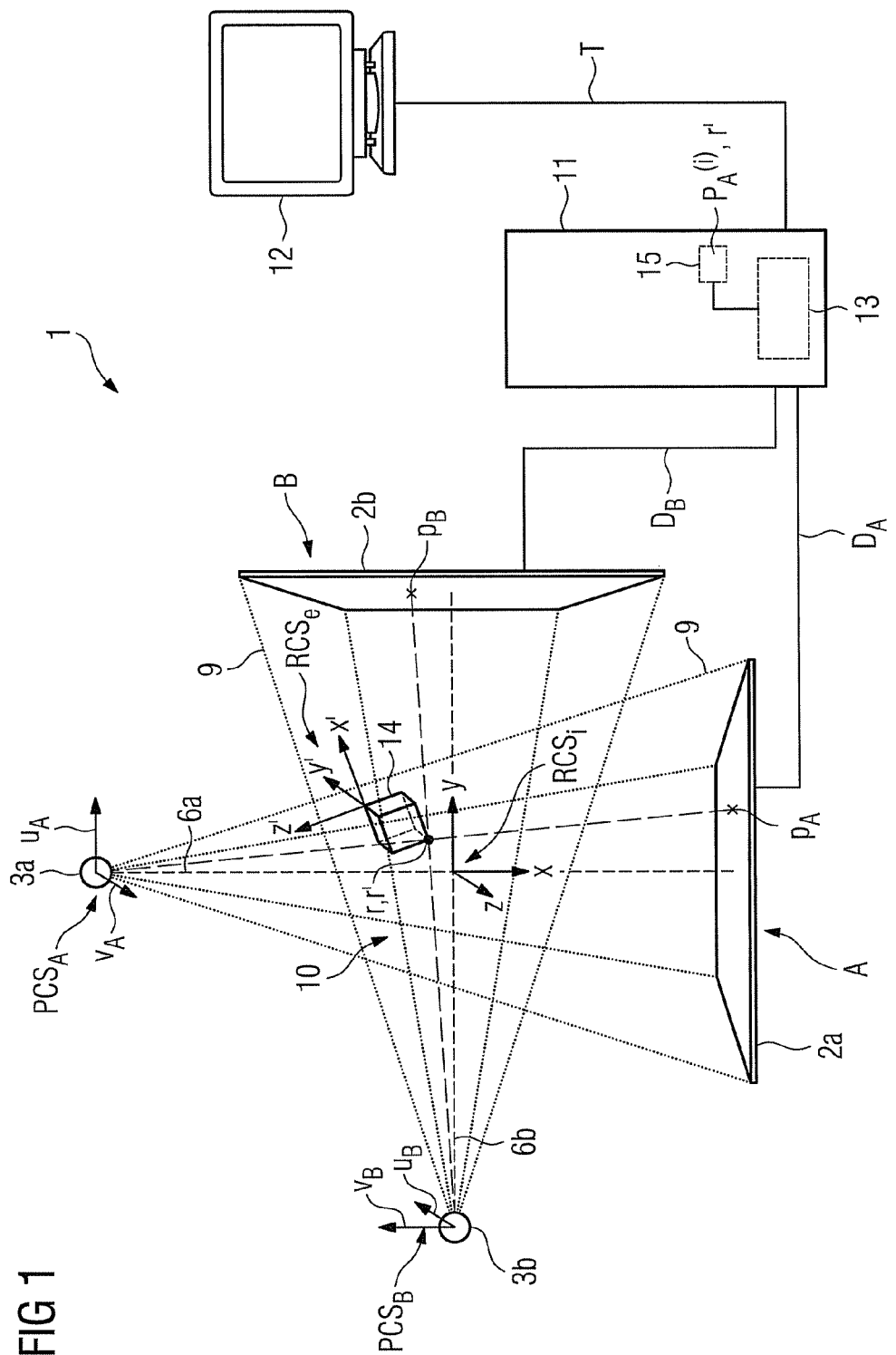
FIG. 1 shows a schematic representation of a bi-plane X-ray unit with a calibration unit which is designed for calibration of the unit by using a static calibration phantom.

FIG. 1 shows a schematic representation of a (bi-plane) X-ray unit 1, in other words an X-ray unit having two radiographic planes A and B arranged offset with respect to one another. With regard to the X-ray unit 1, this is an interventional angiography system having two independently movable C-arms. Such X-ray units are also referred to as bi-plane angiography systems.

Each of the radiographic planes A and B is essentially formed by a two-dimensional X-ray detector 2a or 2b respectively. Additionally associated with each radiographic plane A and B is an X-ray source 3a or 3b respectively. The X-ray detector 2a,2b and the X-ray source 3a,3b for the respective radiographic plane A and B are each mounted opposite one another on a C-arm (not shown). In this situation, the alignment of each radiographic plane A and B in the space is characterized by a central ray 6a,6b in the respective radiographic plane A and B, which connects the respective X-ray source 3a,3b with the respective X-ray detector 2a,2b and in the process is perpendicular to the respective detector surface.

Through the emission of X-rays, by means of each of the two X-ray sources 3a and 3b objects which are situated between the X-ray detectors 2a,2b and the respective associated X-ray sources 3a,3b, can be imaged on the respective X-ray detector 2a or 2b located opposite. The radiographic area of the two radiographic planes A and B is indicated in FIG. 1 by marginal rays 9 illustrated by dotted lines. It is clear from the representation that a common radiographic area 10 which can be imaged by both radiographic planes A and B is formed in a central spatial area.

With regard to each radiographic plane A and B, in each case an associated image coordinate system $PCS_A$ or $PCS_B$ respectively with coordinate axes $u_A$, $v_A$ and $u_B$, $v_B$ respectively is defined. Each coordinate system $PCS_A$, $PCS_B$ characterizes the location of an image point $p_A$, $p_B$ within the respective radiographic plane A, B.

With regard to the X-ray unit 1, an internal (to the unit) spatial coordinate system $RCS_i$ having coordinate axes x,y,z arranged perpendicular to one another is furthermore defined. In this situation, the origin of this spatial coordinate system $RCS_i$ is chosen for reasons of convention in such a manner that it coincides with the point of intersection of the central rays 6a, 6b. In this situation, the coordinate axis x is chosen such that it is directed vertically downwards in the space.

The orientation of the internal spatial coordinate system $RCS_i$ is independent of the rotational position of the C-arms, in other words it remains unaffected by a C-arm rotation. The image coordinate systems $PCS_A$ and $PCS_B$ are by contrast permanently defined with respect to the respective X-ray detector 2a, 2b. They therefore travel with respect to the surrounding space to accompany a gantry rotation.

Each of the two X-ray detectors 2a, 2b is connected to a (control and evaluation) computer 11 of the X-ray unit 1 for the transfer of image data $D_A$ and $D_B$ respectively. In the computer 11, the image data $D_A$, $D_B$ is processed and evaluated. In particular, image processing software implemented in the computer 11 ascertains tomograms T by means of 3D reconstruction from the image data $D_A$ and $D_B$, in other words three-dimensional slice displays of an X-rayed object under examination, in particular of a patient, which can subsequently be displayed for example by way of a screen 12 connected to the X-ray unit 1. Furthermore, navigation software is implemented in the computer 11, which is designed to use the image data $D_A$ and $D_B$ to determine the location of an object imaged therein in the space—in particular in units of the internal spatial coordinate system $RCS_i$.

A precise knowledge of the orientation of the two radiographic planes A and B in the space is required in order to carry out an evaluation of the three-dimensional image information from the image data $D_A$ and $D_B$. This orientation, designated as projection geometry in the following, is ascertained by means of a calibration method described in detail in the following. In order to automatically execute this calibration method the X-ray unit 1 comprises a calibration unit 13, which is realized in the form of a software module in the example illustrated, and a part of the control and evaluation software implemented in the computer 11.

In order to execute the calibration method, with regard to the variant of the X-ray unit 1 represented in FIG. 1 a calibration phantom 14 is additionally required which comprises a plurality of X-ray detectable point objects in a fixed three-dimensional arrangement. According to FIG. 1, the calibration phantom 14 has by way of example the shape of a cube whose eight corners form such a point object for the given situation. Alternatively, it is also possible for example to use a spiral phantom.

With regard to the calibration phantom 14, an external spatial coordinate system $RCS_e$ is defined. This spatial coordinate system $RCS_e$ is formed from three coordinate axes x', y' and z' arranged at right angles, which are aligned in the direction of the edges of the cube-shaped calibration phantom 14. The origin of the spatial coordinate system $RCS_e$ is chosen such that it coincides with a corner of the cube. In principle however, the orientation of the coordinate axes x', y' and z' and also the origin of the spatial coordinate system $RKS_e$ are freely selectable.

The cube corners of the calibration phantom 13 are employed in accordance with the method in order to generate a calibration point in each case. For this purpose, the coordinates of the points in space r' in units of the external spatial coordinate system $RCS_e$ corresponding to the cube corners are stored in a memory 15 of the computer 11 and are thus known.

Internally to the unit, with respect to the radiographic plane A (which can be calibrated in a stable manner) a reference projection geometry is furthermore predefined, for which an internal projection matrix $P_A^{(i)}$ is predefined in the memory 15. The reference projection geometry is advantageously chosen in such a manner that the central ray 6a is perpendicular, in particular directed vertically downwards. This enables a particularly simple and precise hardware calibration of the gantry 5 to the reference projection geometry by aligning the central ray 6a with the direction of gravity.

In the reference projection geometry the projection matrix $P_A^{(i)}$ maps the internal spatial coordinate system $RCS_i$ onto the image coordinate system $PCS_A$ of the radiographic plane A:

$$p_A|_{PCS_A} = P_A^{(i)} \cdot r|_{RCS_i} \qquad \text{GLG 1}$$

In GLG 1, $p_A = (u_A, v_A, 1)^T$ stands for an image point defined in units of the image coordinate system $PCS_A$ and $r = (x,y,z,1)^T$ stands for that point in space defined in units of the spatial coordinate system $RCS_i$ which is projected into the image point $p_A$ when the radiographic plane A is situated in the reference projection geometry. The notation $(\ldots)^T$ describes mathematically the transpose of the parentheses. The variables $p_A$ and $r$ are thus defined as column vectors; $p_A$ and $r$ are written in so-called homogeneous coordinates and accordingly expanded in each case by a formal coordinate having the value 1. The projection matrix $P_A^{(i)}$ accordingly has the dimension 4×3.

In similar fashion to the projection matrix $P_A^{(i)}$, it is also possible to define for the radiographic plane B an internal projection matrix $P_B^{(i)}$ which maps the internal spatial coordinate system $RCS_i$ onto the image coordinate system $PCS_B$, and thus also describes how the point in space r characterized in internal spatial coordinates is projected onto the radiographic plane B:

$$p_B|_{PCS_B} = P_B^{(i)} \cdot r|_{RCS_i} \qquad \text{GLG 2}$$

Again in similar fashion to GLG 1 and 2, it is also possible to define for each of the radiographic planes A and B an external projection matrix $P_A^{(e)}$ or $P_B^{(e)}$ respectively which maps the external spatial coordinate system $RCS_e$ onto the image coordinate systems $PCS_A$ and $PCS_B$ respectively, and thus also describes how the same, but now characterized in external spatial coordinates, point in space $r \rightarrow r' = (x', y', z')$ is projected onto the radiographic planes A and B respectively:

$$p_A|_{PCS_A} = P_A^{(e)} \cdot r'|_{RCS_e} \qquad \text{GLG 3}$$

$$p_B|_{PCS_B} = P_B^{(e)} \cdot r'|_{RCS_e} \qquad \text{GLG 4}$$

The projection matrixes $P_A^{(i)}$, $P_B^{(i)}$, $P_A^{(e)}$ and $P_B^{(e)}$ are defined for the same gantry position, they therefore describe the imaging circumstances for the situation where the radiographic plane A is situated in the reference projection geometry. Whereas the projection matrix $P_A^{(i)}$—as mentioned previously—is already known at the beginning of the method, the remaining projection matrixes $P_B^{(i)}$, $P_A^{(e)}$ and $P_B^{(e)}$ are only ascertained in the course of the method. The purpose of the method in this case is to determine the internal projection matrix $P_B^{(i)}$ as a measure of the positioning of the radiographic plane B with respect to the internal spatial coordinate system $RCS_i$.

In order to perform the calibration it is ensured that the calibration phantom 14 is situated in a fixed position in the common radiographic area 10 of the radiographic planes A and B. Moreover it is ensured that the radiographic plane A is situated in the reference projection geometry.

According to the method, subject to these prerequisites the calibration unit 13 initiates the X-ray photographic capture of the calibration phantom 14 through the two radiographic planes A and B. On the basis of the corresponding image data $D_A$ and $D_B$, by using pattern recognition algorithms the calibration unit 13 ascertains the coordinates of the image points $p_A$ and $p_B$ corresponding to the calibration points (cube corners), in units of the associated image coordinate system $PCS_A$ or $PCS_B$ respectively in each case.

On the basis of these image points $p_A$ and $p_B$ and also on the basis of the stored coordinates of the calibration points (cube corners) with respect to the external coordinate system $PCS_e$, by solving equations GLG 3 and 4 the calibration unit 13 then calculates the external projection matrixes $P_A^{(e)}$ and $P_B^{(e)}$. The calibration unit 13 therefore solves GLG 3 and 4 either mathematically/analytically, for example through interpretation of GLG 3 and 4 as linear systems of equations, or by means of an iterative approximation method.

On the basis of the internal projection matrix $P_A^{(i)}$ and also the external projection matrix $P_A^{(e)}$ the calibration unit 13 then determines a transformation matrix $T^{(e \rightarrow i)}$ which maps the external spatial coordinate system $RCS_e$ onto the internal spatial coordinate system $RCS_i$:

$$P_A^{(i)} = P_A^{(e)} \cdot T^{(e \rightarrow i)} \qquad \text{GLG 5}$$

With regard to the transformation matrix $T^{(e \rightarrow i)}$, this is a rigid-body transform in the form:

$$T^{(e \rightarrow i)} = \begin{pmatrix} R^{(e \rightarrow i)} & t^{(e \rightarrow i)} \\ 0_3^T & 1 \end{pmatrix}^{-1} \qquad \text{GLG 6}$$

where:
  $R^{(e \rightarrow i)}$ stands for a 3×3 rotation matrix which transforms the unit vectors $e_{x'}$, $e_{y'}$ and $e_{z'}$ of the external spatial coordinate system $RCS_e$ into the unit vectors $e_x$, $e_y$ and $e_z$ of the internal spatial coordinate system $RCS_i$,
  $t^{(e \rightarrow i)}$ stands for a three-dimensional column displacement vector which transforms the origin of the external spatial coordinate system $RCS_e$ into the origin of the internal spatial coordinate system $RCS_i$ (FIG. 3) and
  $0_3^T$ stands for a three-dimensional row zero vector.

In this situation the calibration unit 13 determines the transformation matrix $T^{(e \rightarrow i)}$ through approximate or mathematical/analytical solution of equation GLG 5.

Finally, the calibration unit 13 determines the internal projection matrix $P_B^{(i)}$ in accordance with the equation similar to GLG 5

$$P_B^{(i)} = P_B^{(e)} \cdot T^{(e \rightarrow i)} \qquad \text{GLG 5}$$

In a method variant not described in detail it is not a prerequisite that the coordinates of the point objects of the calibration phantom 14 with respect to the external spatial coordinate system $RCS_e$ be known from the outset. Rather, in this case, the calibration unit 13 is additionally designed so as to determine these coordinates initially by means of a triangulation method. In this case, the calibration phantom 14 is mapped on the radiographic plane A under two different—known in each case—projection geometries. From the resulting image data $D_A$ the calibration unit 13 then determines the points in space r' corresponding to the point objects of the calibration phantom 14 with respect to the external spatial coordinate system $RCS_e$, and then executes the method described above.

Figure 2:
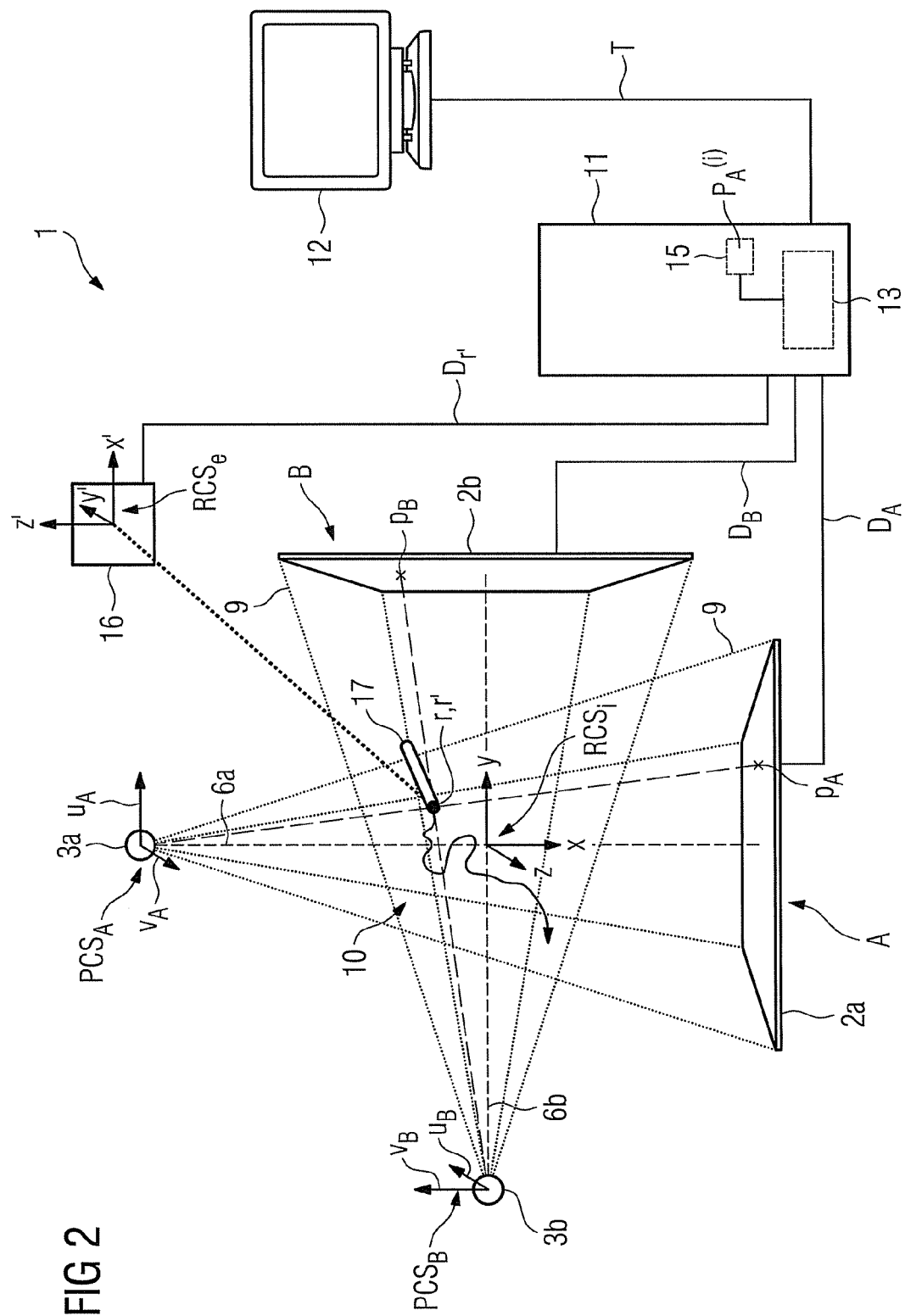
FIG. 2 shows in the representation according to FIG. 1 an alternative embodiment of the bi-plane X-ray unit, in which the calibration unit is designed in order to perform the calibration by using the spatial position of a point object ascertained by an instrument localization device.

A further variant of the bi-plane X-ray unit 1 is illustrated in FIG. 2. In terms of the hardware, the X-ray unit 1 illustrated in FIG. 2 matches the embodiment described in connection with FIG. 1. It differs from the latter in that according to FIG. 2 the calibration unit 13 is however designed to additionally take into consideration the position data $D_{r'}$ delivered by an instrument localization device (referred to in the following as tracking system 16). This enables the calibration to be performed without having to resort to a static calibration phantom.

In order to generate the calibration points, according to FIG. 2 a medical instrument 17, in particular a catheter, is used instead of the calibration phantom 14. This instrument 17 has at least one detection point which can be localized by means of the tracking system 16. The tracking system 16 in question is for example a magnetic tracking system, wherein a spatially inhomogeneous magnetic field is generated in the radiographic area 10 of the X-ray unit 1 by the tracking system 16. In this case, in the detection point of the instrument 17, in the catheter tip for example, is arranged a three-dimensional magnetic sensor which measures the local strength and alignment of the magnetic field and delivers corresponding data back to the tracking system 16. The latter then uses the known spatial magnetic field distribution and the magnetic field strength and alignment measured at the detection point to determine the point in space r' at which the instrument 17 is situated with its detection point. The external spatial coordinate system $RCS_e$ is defined here by the tracking coordinate system 16. The coordinates of the point in space r' are ascertained accordingly in units of this spatial coordinate system $RCS_e$ and passed to the computer 11 of the X-ray unit 1.

For calibration of the X-ray unit 1, the X-ray unit 1 is in turn set up such that the radiographic plane A is situated in the reference projection geometry, for which the internal projection matrix $P_A^{(i)}$ is predefined internally to the device. The instrument 17 is then moved through the common radiographic area 10 of the radiographic planes A and B. In this situation, image data $D_A$ and $D_B$ from the instrument 17 is captured simultaneously by means of the two radiographic planes A and B at a plurality of successive points in time. At each of these capture points in time, the coordinates of the current point in space r' in the external spatial coordinate system $RKS_e$, at which the detection point of the instrument 17 is situated, continue to be ascertained by means of the tracking system 16. Each of these snapshots in turn yields a calibration point for the remainder of the method.

In this situation, at least 6 such calibration points are captured. On the basis of these calibration points and the known internal projection matrix $P_A^{(i)}$, in similar fashion to the method described in connection with FIG. 1 the calibration unit 13 ascertains the internal projection matrix $P_B^{(i)}$ for the radiographic plane B. If the internal camera parameters are known, the minimum number of calibration points required is reduced to 3.

Figure 3:
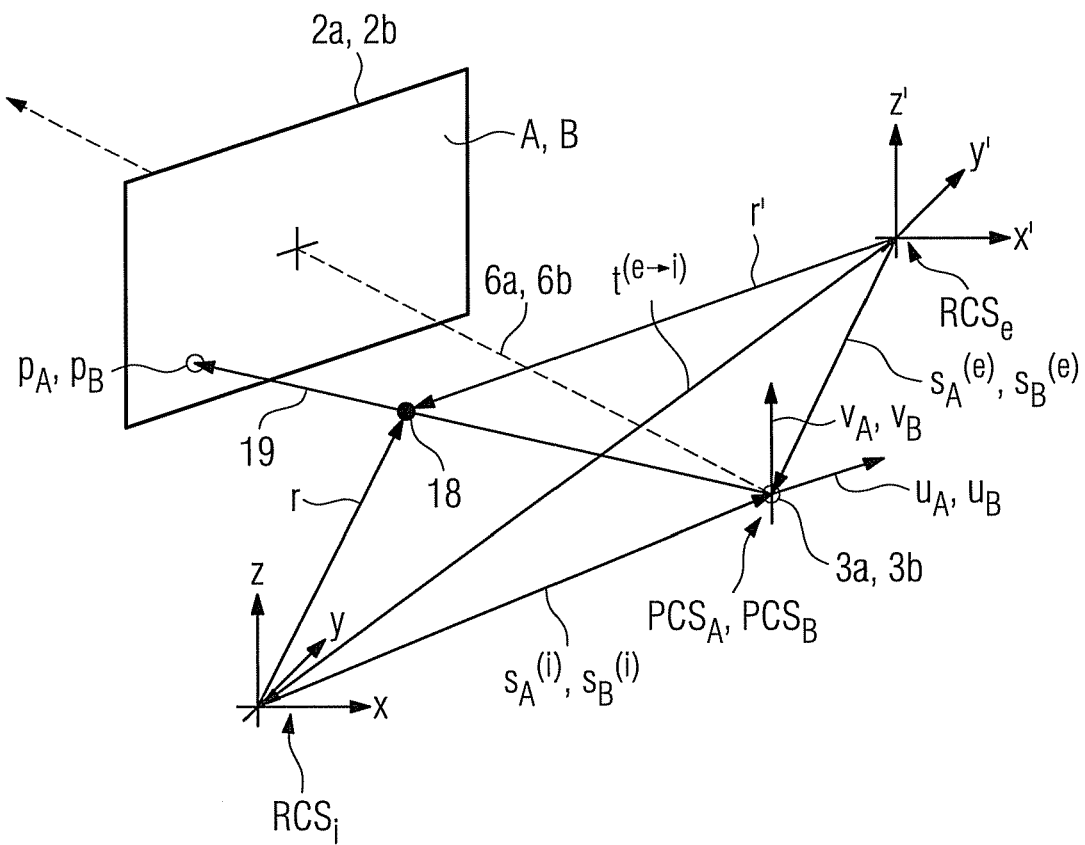
FIG. 3 shows a schematic representation of the vectorial relationships of a spatial coordinate system internal to the unit, a spatial coordinate system external to the unit and an image coordinate system of an radiographic plane of the unit according to FIG. 1 or FIG. 2.

The mathematical relationship of the coordinate systems $RCS_i$, $RCS_e$ and $PCS_A$ or $PCS_B$ is illustrated in detail in FIG. 3. FIG. 3 shows a schematic representation of one radiographic plane (in which case this can be either of the radiographic planes A or B) with the associated X-ray detector 2*a* or 2*b* and the associated X-ray source 3*a* or 3*b*. FIG. 3 additionally shows the image coordinate system $PCS_A$ or $PCS_B$ and also the two spatial coordinate systems $RCS_i$ and $RCS_e$. Finally, FIG. 3 shows an image ray 19 connecting the X-ray source 3*a* or 3*b* by way of a point object 18 with the corresponding image point $p_A$ or $p_B$ v. Furthermore, in FIG. 3 r designates the position vector of the point object 18 in units of the internal spatial coordinate system $RCS_i$, r' designates the position vector of the spatial object 18 in units of the external spatial coordinate system $RCS_e$, $t^{(e \to i)}$ designates the offset vector mapping the origin of the spatial coordinate system $RCS_e$ to the origin of the spatial coordinate system $RCS_i$, $s_A^{(i)}$ and $s_B^{(i)}$ designate an offset vector mapping the origin of the spatial coordinate system $RCS_i$ to the origin of the image coordinate system $PCS_A$ or $PCS_B$ respectively and $s_A^{(e)}$ and $s_B^{(e)}$ designate an offset vector mapping the origin of the spatial coordinate system $RCS^e$ to the origin of the image coordinate system $PCS_A$ or $PCS_B$ respectively.

With the stable first radiographic plane A of the X-ray unit 1, in particular a 3D image data set (tomogram) can be generated which is scaled in units of the internal spatial coordinate system $RCS_i$. Points which are localized with the aid of the two radiographic planes A and B of the X-ray unit 1 can likewise be specified in units of the internal spatial coordinate system $RCS_i$ because of the calibration of the radiographic plane B described above. Such points can thus be represented in the 3D image data set—for example in the volume or on surfaces of the three-dimensional image information.

The invention claimed is:

1. A method for calibrating a multi-plane X-ray unit, comprising:

setting a reference projection geometry with respect to a first radiographic plane of the unit;

defining an internal projection matrix of the first radiographic plane for mapping a spatial coordinate system internal to the unit onto an image coordinate system of the first radiographic plane in the reference projection geometry;

capturing a first image data at a plurality of calibration points by the first radiographic plane in the reference projection geometry;

determining an external projection matrix of the first radiographic plane for mapping a spatial coordinate system external to the unit onto the image coordinate system of the first radiographic plane based on the first image data and coordinates of the calibration points;

capturing a second image data at the calibration points by a second radiographic plane of the unit;

determining an external projection matrix of the second radiographic plane for mapping the spatial coordinate system external to the unit onto an image coordinate system of the second radiographic plane based on the second image data and the coordinates of the calibration points; and determining a measure of a position of the second radiographic plane based on the internal projection matrix and the external projection matrix of the first radiographic plane as well as the external projection matrix of the second radiographic plane.

2. The method as claimed in claim 1, wherein a static calibration phantom having a plurality of X-ray detectable point objects is employed for generating the calibration points.

3. The method as claimed in claim 2, wherein coordinates of the X-ray detectable point objects in the static calibration phantom are predefined in the external spatial coordinate system.

4. The method as claimed in claim 2, wherein coordinates of the X-ray detectable point objects in the static calibration phantom with respect to the external spatial coordinate system are determined through a triangulation from the first image data under two different projection geometries.

5. The method as claimed in claim 1, wherein an object is moved in a common radiographic area of the first and the second radiographic planes and a location of the object is detected by a localization device for generating the calibration points.

6. The method as claimed in claim 5, wherein a coordinate of the object with respect to the external spatial coordinate system is determined based on the location of the object and image data of the object captured by the first and the second radiographic planes.

7. The method as claimed in claim 1, wherein a transformation rule for mapping the spatial coordinate system external to the unit and the spatial coordinate system internal to the unit onto one another is calculated from the internal projection matrix and the external projection matrix of the first radiographic plane.

8. The method as claimed in claim 1, wherein an internal projection matrix of the second radiographic plane for mapping the spatial coordinate system internal to the unit onto the image coordinate system of the second radiographic plane is calculated as the measure of the position of the second radiographic plane.

9. The method as claimed in claim 1, wherein the measure of the position of the second radiographic plane is determined with respect to the spatial coordinate system internal to the unit.

10. The method as claimed in claim 1, wherein the measure of the position of the second radiographic plane is determined with respect to the first radiographic plane.

11. A device for calibrating a multi-plane X-ray unit, comprising:
    a calibration unit that:
        sets a reference projection geometry with respect to a first radiographic plane of the unit;
        defines an internal projection matrix of the first f radiographic plane for mapping a spatial coordinate system internal to the unit onto an image coordinate system of the first radiographic plane in the reference projection geometry;
        determines an external projection matrix of the first radiographic plane for mapping a spatial coordinate system external to the unit onto the image coordinate system of the first radiographic plane based on a first image data and coordinates of calibration points, the first image data being captured by the first radiographic plane in the reference projection geometry at the calibration points;
        determines an external projection matrix of the second radiographic plane for mapping the spatial coordinate system external to the unit onto an image coordinate system of the second radiographic plane based on a second image data captured by the second radiographic plane at the calibration points and the coordinates of the calibration points; and
        determines a measure of a position of the second radiographic plane based on the internal projection matrix and the external projection matrix of the first radiographic plane as well as the external projection matrix of the second radiographic plane.

12. A multi-plane X-ray unit, comprising:
a first radiographic plane that captures a first image data in a reference projection geometry of the first radiographic plane at a plurality of calibration points;
a second radiographic plane arranged offset with respect to the first radiographic plane that captures a second image data at the calibration points; and
a calibration unit that:
    sets the reference projection geometry,
    defines an internal projection matrix of the first f radiographic plane for mapping a spatial coordinate system internal to the unit onto an image coordinate system of the first radiographic plane in the reference projection geometry,
    determines an external projection matrix of the first radiographic plane for mapping a spatial coordinate system external to the unit onto the image coordinate system of the first radiographic plane based on the first image data and coordinates of the calibration points,
    determines an external projection matrix of the second radiographic plane for mapping the spatial coordinate system external to the unit onto an image coordinate system of the second radiographic plane based on the second image data and the coordinates of the calibration points, and
    determines a measure of a position of the second radiographic plane based on the internal projection matrix and the external projection matrix of the first radiographic plane as well as the external projection matrix of the second radiographic plane.

* * * * *